United States Patent [19]
van der Stoel

[11] Patent Number: 4,730,043
[45] Date of Patent: Mar. 8, 1988

[54] PROCESS FOR PREPARING PYRIMIDINE

[75] Inventor: Roland E. van der Stoel, Buchten, Netherlands

[73] Assignee: Stamicarbon B.V. Licensing Subsidiary of DSM, Geleen, Netherlands

[21] Appl. No.: 812,812

[22] Filed: Dec. 23, 1985

Related U.S. Application Data

[63] Continuation-in-part of Ser. No. 652,472, Sep. 20, 1984, abandoned.

[30] Foreign Application Priority Data

Oct. 7, 1983 [NL] Netherlands ............... 8303449

[51] Int. Cl.$^4$ ........................................ C07D 239/26
[52] U.S. Cl. ........................................... 544/242
[58] Field of Search ...................... 544/242; 546/349

[56] References Cited

U.S. PATENT DOCUMENTS

| | | | |
|---|---|---|---|
| 3,050,523 | 8/1962 | Erner et al. | 544/242 |
| 3,334,101 | 8/1967 | Myerly et al. | 546/349 X |
| 3,689,491 | 9/1972 | Suvorov et al. | 546/349 |
| 4,118,388 | 10/1978 | Yokoyama et al. | 546/349 |

FOREIGN PATENT DOCUMENTS

| | | | |
|---|---|---|---|
| 0137567 | 4/1985 | European Pat. Off. | 544/242 |
| 0400187 | 4/1976 | U.S.S.R. | 546/349 |

OTHER PUBLICATIONS

Dunn, et al., Chemical Abstracts, vol. 87, 151331f (1977).
Suvorov, et al., Chemical Abstracts, vol. 94, 83899q (1981).
Glubokovskikh, et al., Chemical Abstracts, vol. 94, 156714n (1981).
Glubokovskikh, et al., Chemical Abstracts, vol. 94, 174818d (1981).
Daicel Chemical Industries, Chemical Abstracts, vol. 96, 35109b (1982).
D. J. Brown "Pyrimidine and Its C-Alkyl and C-Aryl Derivatives" vol. 16, 1962, pp. 116–117, *Interscience Publishers*.
D. J. Brown "(Supplement I) Pyrimidine and Its C-Alkyl and C-Aryl Derivatives (H 116)" 1970, p. 86, Wiley-Interscience Publication.
D. J. Brown "(Supplement II) Pyrimidine and Its C-Alkyl and C-Aryl Derivatives (H 116, E86)" 1985, p. 109, *Interscience Publication*.
Chemische Berichte, 84 pp. 452–453, 1951 "Oxydation Von Pyridinhomologen in Der Gasphase".
D. J. Brown, *1962 Monograph* pp. 120–121; Alkylpyrimidine Compounds.
Chemische Brochure, 93 pp. 1402–1406, 1960 "Synthese Von Pyrimidinen Mittels Tris-Formaamino-Methans".
C. J. Kim "Noble Metal-Catalyzed Water-Hydrocarbon Reaction Paths" Journal of Cytalysts 52, 169–175 (1978).

*Primary Examiner*—Donald G. Daus
*Assistant Examiner*—D. Rivers
*Attorney, Agent, or Firm*—Carl G. Love

[57] ABSTRACT

Alkylpyrimidines are dealkylated to the corresponding pyrimidines by contacting with an oxidation catalyst containing one or more oxides of at least one of the elements of the group consisting of Bi, Mo and V in the presence of water and oxygen in the gas phase at a temperature of 300°–450° C.

7 Claims, No Drawings

PROCESS FOR PREPARING PYRIMIDINE

The invention relates to a process for preparing pyrimidine. Pyrimidine is used, among other things, as raw materials for preparing crop protection chemicals. In Chemische Berichte 91 (1958), pages 2832-2849, a laboratory synthesis for pyrimidine is described. 1-methoxy-1,3,3-triethoxypropane is reacted at 208° C. with a 6 to 10 fold excess of formamide. The yield of pyrimidine then formed is 72 mole % calculated in respect of moles 1-methoxy-1,3,3-triethoxypropane. The disadvantage of such a synthesis lies in expensive raw materials, the necessity of a large excess of formamide and a relatively low yield of 28 wt % when calculated as a percentage of the weight of 1-methoxy-1,3,3-triethoxypropane.

The object of the invention is a commercially attractive process for preparing pyrimidine.

According to the present invention pyrimidine is prepared from an alkyl-substituted pyrimidine by contacting the latter in the gas phase at a temperature of 300°-450° C. with an oxidation catalyst containing one or more oxides of at least one of the elements of the group consisting of Bi, Mo and V, and in the presence of water and of a gas containing molecular oxygen. Pyrimidine is recovered from the reaction products mixture at high conversion levels.

This invention provides a completely new type of reaction. Unexpectedly, the use of water in the reaction system at the high temperatures used does not preclude the synthesis of pyrimidine.

Oxidation and ammoxidation represent a large class of reactions, in which a large group of raw materials can be employed. It is, however, always unexpected whether the use of a new type of starting compound will thereby give rise to a useful, easy obtainable end-product.

For instance pyridines are very different from pyrimidines in stability with respect to water or heat. Even within the class of pyridines, problems arise when dealkylating groups are substituted at different places on the ring.

This new process now makes it possible for pyrimidine to be prepared in a practical manner, starting from cheap raw materials which are available on a large scale. Thus, for instance, in the prior art the preparation of 2-methylpyrimidine in a high yield has been described using as starting materials 1,3-diaminopropane and acetaldehyde, see Yakugaku Zasshi 96, pages 1005-1012 (1976); further the preparation of 2-ethyl-pyrimidine is described by, inter alia, the dehydrocyclodimerisation of 1,3-diaminopropane as described in Yakugaku Zasshi 96, pages 801-809 (1976).

In the process according to the present invention alkyl-pyrimidines with substituents preferably in the 2 and/or 4 (6) positions are used as starting materials. The alkyl group(s) preferably contain(s) 1–4 C atoms such as, for instance, 4-methylpyrimidine and 2-ethylpyrimidine, and particularly 2-methylpyrimidine.

The catalyst used in this invention is the same type of catalyst already known for selective oxidation or ammoxidation of hydrocarbons and which contains one or more oxides of one or more of the following elements: Bi, Mo and V. Because the oxidation state of the metals changes during the oxidation reactions, it is not significant to specify the same.

The metal oxide catalyst can be used on a carrier material, known per se. Such carriers may contain, for instance, silicon oxide and/or aluminium oxide. Catalysts on a carrier normally contain between 1 and 40% by weight of the metal, preferably between 4 and 25% by weight.

The process according to the invention can be carried out at an elevated temperature in the range of 200°-550° C., with preference given to a temperature of 300°-450° C., advantageously from 320° to 400° C.

The process according to the invention, in which the alkyl substituent(s) is (are) oxidized, is carried out in the presence of water and a gas containing molecular oxygen. The object of the presence of water is to confine the oxidation to the alkyl substituent(s). Generally at least 5 moles water are used per mole substituted pyrimidine, advantageously more than 10 moles of water.

For economic reasons the gas containing molecular oxygen is preferably air. For the oxidation reaction of 2-methylpyrimidine a stoichiometric amount of 1.5 moles, preferably 3 moles, oxygen is required per mole of substituted pyrimidine. If air is used as a gas containing molecular oxygen, these amounts correspond with 7.5 and 15 moles air, respectively. In what follows hereafter 1 mole oxygen has been taken, for reasons of simplicity, to equal 5 moles air. If the substituted pyrimidine contains more than one methyl substituent, or if the alkyl group(s) contain(s) more than one C atom, a corresponding amount of extra oxygen may be required for carrying out the process. However, less oxygen may also be used, but then the conversion will be reduced.

The upper limit of the excess of water is not critical and is determined mainly by the contents of the reactor and by the desired period of contact. Neither does a maximum exist for the upper limit of the quantity of air, but here should be remembered that too large a quantity of air may result in a lower selectivity. Preferably at least 15 moles water and at least 20 moles air are used per mole alkyl-substituted pyrimidine.

For the practical realization of the process according to the invention, the techniques already known per se for the realization of gas phase reactions may be used. For instance the gaseous starting mixture may be passed over the catalyst in the form of a fixed bed or a so-called fluidized bed. The space velocity can be varied, for instance between 0.001 and 2 g starting compound per milliliter catalyst material (bulk volume) per hours. The pressure at which the reaction takes place in the gas phase is not important as such; accordingly the reaction is generally carried out at autogenous pressure.

The further processing and recovery of the pyrimidine product obtained in the reaction mixture can be effected in a manner known per se by cooling and by subsequently carrying out, for instance, a distillation, an extraction or a crystallization process.

The invention is further elucidated in the following examples.

EXAMPLE I

Through a vertical tubular reactor (diameter 17 mm, length 400 mm) containing a zone of 10 ml (bulk volume) catalyst and provided with a heating jacket, a gaseous mixture of 2-methylpyrimidine, water and air was passed from top to bottom. Per mole 2-methylpyrimidine 17 moles water and 45 moles air were used. The catalyst used was $V_2O_5$ on a carrier of $\alpha$-alumina with a specific surface of 25–35 $m^2/g$ (10% (wt) V calculated as metal in respect of the total quantity of catalyst). Per ml (bulk volume) catalyst 0.18 g 2-methylpyrimidine was passed through per hour. The temperature of the heating jacket was varied (see Table 1). The heat developed during the exothermic reaction caused a higher temperature in the zone containing the catalyst.

After an operating period of 2 hours the reaction conditions were kept constant for 1 hour and the reaction mixture obtained during this period was cooled to 12° C. The composition of the then condensed product was determined by gas chromatography. From this determination and from the weight of the quantity of 2-methylpyrimidine that had been passed over in the said period of 1 hour, the conversion of 2-methylpyrimidine and the selectivity to pyrimidine could be calculated.

The conversion is understood to mean the amount of 2-methylpyrimidine converted (amount of 2-methylpyrimidine passed over less the amount of 2-methylpyrimidine in the condensed product), expressed in percentages of the amount of 2-methylpyrimidine passed over. The selectivity to pyrimidine is understood to mean the amount of pyrimidine that can theoretically be formed from the amount of 2-methylpyrimidine converted. The results are mentioned in Table 1.

EXAMPLE II-VII

The process according to Example I was followed with the understanding that, instead of an operating period of 2 hours, an operating period of respectively 4, 5.5, 7, 9, 11 and 14 hours was applied, before the 1 hour measurement was started. In scrutinizing these experiments, it must be borne in mind, that the results are virtually not influenced by the period of time that the catalyst was used.

The results of Examples II-VII are summarized in Table 1.

TABLE 1

| Example | I | II | III | IV | V | VI | VII |
|---|---|---|---|---|---|---|---|
| operating period in hours | 2 | 4 | 5.5 | 7 | 9 | 11 | 14 |
| temperature of the heating jacket (°C.) | 410 | 380 | 360 | 340 | 320 | 300 | 260 |
| temperature of the catalyst zone (°C.) | 447 | 404 | 383 | 359 | 333 | 309 | 262 |
| conversion 2-methylpyrimidine (%) | 94 | 84 | 81 | 75 | 69 | 44 | 21 |
| selectivity pyrimidine (%) | 32 | 46 | 53 | 55 | 50 | 56 | 33 |

As is clear from these examples, a higher temperature gives rise to a higher conversion although at the expense of selectivity. Under the here performed conditions, a temperature range of 320-380 appears to be optimal.

EXAMPLES VIII-X

In the manner described in Example I, 2-methylpyrimidine was dealkylated at a heating jacket temperature of 380° C., using 17 moles of water per mole of 2-methylpyrimidine, while the amount of air supplied was varied. The results are summarized in Table 2.

TABLE 2

| Example | VIII | IX | X |
|---|---|---|---|
| operating period in hours | 7 | 19 | 21 |
| air/2-methylpyrimidine ratio (mole/mole) | 21 | 30 | 42 |
| temperature of the catalyst zone (°C.) | 390 | 395 | 405 |
| conversion 2-methylpyrimidine (%) | 23 | 50 | 89 |

TABLE 2-continued

| Example | VIII | IX | X |
|---|---|---|---|
| selectivity pyrimidine (%) | 76 | 81 | 39 |

From these experiments, it is clear that a lower air supply gives rise to a lower conversion; a very high supply however results in a lower selectivity.

EXAMPLES XI-XIII

In the manner described in Example I, 2-methylpyrimidine was dealkylated at a heating jacket temperature of 380° C., using 45 moles of air per mole of 2-methylpyrimidine, while an amount of water supplied was varied.

At the same time extra nitrogen was supplied in order to keep the period of contact constant.

The results are summarized in Table 3, showing good results at all supplying ratios.

TABLE 3

| Example | XI | XII | XIII |
|---|---|---|---|
| operating period in hours | 4 | 6 | 11 |
| water/2-methylpyrimidine ratio (mole/mole) | 10 | 15 | 25 |
| nitrogen/2-methylpyrimidine ratio (mole/mole) | 9 | 4 | 0 |
| conversion 2-methylpyrimidine (%) | 70 | 31 | 50 |
| selectivity pyrimidine (%) | 61 | 89 | 87 |

EXAMPLES XIV-XVIII

In the manner described in Example I, 2-methylpyrimidine was dealkylated, while the catalyst used was $V_2O_5$ with $KHSO_4$ on α-alumina with a specific surface of $12\pm4$ m$^2$/g (5% (wt) V and 6.7% (wt) $KHSO_4$). Per ml (bulk volume) catalyst 0.19 g 2-methylpyrimidine was used. Per mole 2-methylpyrimidine 19 moles water and 41 moles air were supplied. The temperature was varied as indicated. The results are summarized in Table 4. Again, the results are not dependent on the operating period. It is shown, that with this $V_2O_5$ catalyst also, good results are obtained.

TABLE 4

| Example | XIV | XV | XVI | XVII | XVIII |
|---|---|---|---|---|---|
| operating period in hours | 11.5 | 14.5 | 20.5 | 24 | 26 |
| heating jacket temperature (°C.) | 325 | 350 | 375 | 385 | 400 |
| conversion 2-methylpyrimidine (%) | 52 | 69 | 79 | 79 | 81 |
| selectivity pyrimidine (%) | 74 | 71 | 58 | 57 | 52 |

EXAMPLES XIX-XXIII

In the manner described in Example I, 2-methylpyrimidine was dealkylated, while 10 ml of a catalyst was used containing the elements Bi and Mo (4.4 wt % Bi and 20.4 wt % Mo calculated as metals in respect of the total amount of catalyst) on an $SiO_2$ carrier. This catalyst was prepared by mixing 22.4 g phosphomolybdic acid. $H_3PO_4.12MoO_3.24H_2O$ with 2.47 g 85% (wt) orthophosphoric acid, 5.7 g bismuth nitrate $Bi(NO_3)_3.5$-$H_2O$ and 38 g $SiO_2$ (the trade product aerosil). The thus resulting mixture was calcined at 660° C.

The temperature of the heating jacket and the amount of air supplied were varied. The results are summarized in Table 5. Obviously, experiment XXII shows the best performance with this catalyst, indicating, that a higher amount of air has a positive effect on the yield obtained.

TABLE 5

| Example | XIX | XX | XXI | XXII | XXIII |
|---|---|---|---|---|---|
| operating period in hours | 1 | 2.5 | 5 | 9 | 11 |
| heating jacket temperature (°C.) | 380 | 380 | 380 | 380 | 400 |
| temperature catalyst zone (°C.) | 398 | 401 | 403 | 405 | 416 |
| air/2-methylpyrimidine ratio (mole/mole) | 23 | 30 | 35 | 45 | 23 |
| conversion 2-methyl-pyrimidine (%) | 48 | 62 | 66 | 97 | 41 |
| selectivity pyrimidine (%) | 93 | 87 | 72 | 79 | 81 |

EXAMPLES XXIV–XXVII

With the catalyst as used in Examples XIX–XII, a gaseous mixture of 2-ethylpyrimidine, water and air was dealkylated. Per ml (bulk volume) catalyst 0.13 g 2-ethylpyrimidine was passed through per hour. Per mole 2-ethylpyrimidine 27 moles water were used. The heating jacket temperature was 380° C. The amount of air supplied was varied.

The results, summarized in Table 6, show that this alkylpyrimidine is also dealkylated with this process in a high yield, and that a high ratio of air to 2-ethylpyrimidine favors a higher conversion.

TABLE 6

| Example | XXIV | XXV | XXVI | XXVII |
|---|---|---|---|---|
| operating period in hours | 1 | 2.5 | 4 | 9 |
| air/2-ethylpyrimidine ratio (mole/mole) | 30 | 35 | 40 | 45 |
| conversion 2-ethylpyrimidine % | 50 | 66 | 85 | 97 |
| selectivity pyrimidine % | 85 | 72 | 71 | 79 |

EXAMPLE XXVIII

With the $V_2O_5$ catalyst as used in Examples XIV–XVIII, a gaseous mixture of 4-methylpyrimidine, water and air was dealkylated. Per ml (bulk volume) 0.18 g 4-methylpyrimidine was passed through per hour. Per mole 4-methylpyrimidine 17 moles water and 40 moles air were used. The temperature of the heating jacket was 380° C. After an operating period of 4 hours the resulting conversion of 2-methylpyrimidine was 92% and the selectivity to pyrimidine 39%.

EXAMPLE XXIX

In the manner described in Example I, a gaseous mixture of 2-methylpyrimidine, water and air was converted. However per mole (bulk volume) catalyst 0.095 g 2-methylpyrimidine was passed through per hour. The temperature of the heating jacket was 380° C. After an operating period of 1.5 hours the resulting conversion of 2-methylpyrimidine was 81% and the selectivity to pyrimidine 66%.

As the foregoing examples demonstrate, the novel process of this invention provides for the economic production of pyrimidine from a relatively inexpensive starting material, alkyl-substituted pyrimidines, and it is operative under a wide variety of conditions with desirably high ultimate yields.

What is claimed is:

1. Process for preparing pyrimidine, which comprises contacting an alkyl pyrimidine, having an alkyl substituent, of from 1 to 4 carbon atoms, at the 2 and/or 4 (6) position, in the gas phase at a temperature of 300°–450° C. with an oxidation catalyst containing one or more oxides of at least one of the elements of the group consisting of Bi, Mo and V and in the presence of water and of a gas containing molecular oxygen and recovering pyrimidine from the resulting reaction mixture.

2. Process according to claim 1, wherein air is used as gas containing molecular oxygen.

3. Process according to claim 1, wherein the catalyst contains 4–25% by weight of said metal on a carrier composed of alumina or silicon oxide.

4. Process according to claim 1, wherein said contact with the catalyst takes place at a temperature of 320°–400° C.

5. Process according to claim 1, wherein per mole alkyl-substituted pyrimidine at least 15 moles water are used.

6. Process according to claim 1, wherein per mole alkyl-substituted pyrimidine at least 20 moles air are used.

7. Process according to claim 1, wherein 2-methylpyrimidine is used as said alkyl-substituted pyrimidine.

* * * * *